United States Patent [19]

Spears

[11] Patent Number: 5,199,951
[45] Date of Patent: Apr. 6, 1993

[54] METHOD OF DRUG APPLICATION IN A TRANSPORTING MEDIUM TO AN ARTERIAL WALL INJURED DURING ANGIOPLASTY

[75] Inventor: James R. Spears, Bloomfield Hills, Mich.

[73] Assignee: Wayne State University, Detroit, Mich.

[21] Appl. No.: 759,223

[22] Filed: Sep. 13, 1991

Related U.S. Application Data

[63] Continuation-in-part of Ser. No. 525,104, May 17, 1990, Pat. No. 5,092,841.

[51] Int. Cl.$^5$ .............................................. A61M 29/00
[52] U.S. Cl. ...................................... 604/96; 604/113; 606/194; 623/12; 128/400; 128/401
[58] Field of Search .......................... 604/96, 101, 113; 606/7, 8, 13–15, 192–195; 600/36; 623/1, 12; 128/395, 397, 398–401, 402

[56] References Cited

U.S. PATENT DOCUMENTS

5,092,841  3/1992  Speers ............................... 606/194

Primary Examiner—C. Fred Rosenbaum
Assistant Examiner—Chalin Smith
Attorney, Agent, or Firm—Brooks & Kushman

[57] ABSTRACT

A method for treating a lesion (27) in an arterial wall (28) having plaque (52) thereon and a luminal surface (29). The arterial wall (28) has typically been mechanically injured during an angioplasty procedure. As a result of that procedure, the arterial wall (28) and the plaque (52) include fissures (24) defined therein. It has been found that those fissures (24) form excellent sites at which a bioprotective material (26) may become bonded upon application of thermal energy. The method comprising the steps of positioning an angioplasty catheter (20) adjacent to the lesion (27) being treated; delivering a soluble sleeve containing bioprotective material (26) between the arterial wall (28) and the angioplasty catheter (20) so that the bioprotective material (26) is entrapped therebetween applying thermal energy to the lesion (27), thereby liquifying the sleeve and bonding the bioprotective material (26) to the arterial wall (28) and within the fissures (24); removing the angioplasty catheter (20), the bioprotective material (26) remaining adherent to the arterial wall (28) and within the fissures (24); cooling the sleeve so that it becomes solidified; releasing and removing the angioplasty catheter (20) from the site being treated, whereupon the soluble sleeve is irrigated away by blood (50) flowing adjacent thereto, leaving an insoluble material semi- or permanently bonded to the fissures (24) of the arterial wall (28), despite contact with blood (50) flowing adjacent thereto.

63 Claims, 3 Drawing Sheets

FIG.4E

METHOD OF DRUG APPLICATION IN A TRANSPORTING MEDIUM TO AN ARTERIAL WALL INJURED DURING ANGIOPLASTY

STATEMENT OF FEDERALLY SPONSORED RESEARCH

The funding for work described herein was provided in part by the Federal Government, under a grant from the National Institute of Health. The government may have certain rights in this invention.

CROSS-REFERENCE TO RELATED APPLICATION

This is a continuation-in-part of application Ser. No. 525,104 filed May 17, 1990 now U.S. Pat. No. 5,092,841.

TECHNICAL FIELD

This invention relates to angioplasty, and more particularly to a method for treating an arterial wall injured during angioplasty.

BACKGROUND ART

Atherosclerosis is a progressive disease wherein fatty, fibrous, calcific, or thrombotic deposits produce atheromatous plaques, within and beneath the intima which is the innermost layer of arteries. Atherosclerosis tends to involve large and medium sized arteries. The most commonly affected are the aorta, iliac, femoral, coronary, and cerebral arteries. Clinical symptoms occur because the mass of the atherosclerotic plaque reduces blood flow through the afflicted artery, thereby compromising tissue or organ function distal to it.

The mortality and morbidity from ischemic heart disease results primarily from atheromatous narrowings of the coronary arteries. Although various medical and surgical therapies may improve the quality of life for most patients with coronary atherosclerosis, such therapies do not favorably change the underlying anatomy responsible for the coronary luminal narrowings. Until recently, there has not been a non-surgical means for improving the perfusion of blood through the lumina of coronary arteries compromised by atheromatous plaque.

Percutaneous transluminal coronary angioplasty has been developed as an alternative, non-surgical method for treatment of coronary atherosclerosis. During cardiac catheterization, an inflatable balloon is inserted in a coronary artery in the region of coronary narrowing. Inflation of the balloon for 15-30 seconds results in an expansion of the narrowed lumen or passageway. Because residual narrowing is usually present after the first balloon inflation, multiple or prolonged inflations are routinely performed to reduce the severity of the residual stenosis or tube narrowing. Despite multiple or prolonged inflations, a mild to moderately severe stenosis usually is present, even after the procedure is otherwise performed successfully.

The physician will often prefer not to dilate lesions that are not severe because there is a good chance that they will recur. Because the occlusion recurs frequently, conventional angioplasty is often considered to be a suboptimal procedure. As a result, it is sometimes attempted only when a patient does not wish to undergo major cardiac surgery.

There are several reasons why the lesions reappear. One is that small clots form on the arterial wall. Tears in the wall expose blood to foreign material and proteins, such as collagen, which are highly thrombogenic. Resulting clots can grow gradually, or can contain growth hormones which are released by platelets within the clot. Additionally, growth hormones released by other cells, such as macrophages, can cause smooth muscle cells and fibroblasts in the region to multiply. Further, there is often a complete loss of the normal single layer of cells constituting the endothelial lining following angioplasty. This layer normally covers the internal surface of all vessels, rendering that surface compatible, i.e. non-thrombogenic and non-reactive with blood. Mechanically, when an angioplasty balloon is inflated, the endothelial cells are torn away. Combination of the loss of the endothelial layer and tearing within the wall often generates a surface which is quite thrombogenic.

Prior art angioplasty procedures also produce injuries in the arterial wall which become associated with inflammation. White cells will migrate to the area and will lay down scar tissue. Any kind of inflammatory response may cause the growth of new tissue. Restenosis or recurrence of the obstruction results because the smooth muscle cells which normally reside within the arterial wall proliferate. Such cells migrate to the area of the injury and multiply in response thereto.

It therefore appears that in order to combat problems associated with cumulating plaque, attention must be paid to: (1) the importance of thrombus; (2) inflammatory changes; and (3) proliferation. Any combination of these factors probably accounts for most cases of restenosis.

In order to address such problems, the cardiology community needs to administer drugs which are biocompatible and not induce toxic reactions. Therefore, it would be helpful to invoke a technique which allows localized administration of drugs that counteract clotting, interfere with inflammatory responses, and block proliferative responses. However, many such drugs when administered are toxic and are associated with potentially serious side effects which make the treatment and prevention of restenosis impractical. Accordingly, even though there is a number of potentially useful drugs, there is a tendency to avoid using them.

One of the other major problems with conventional methods of treatment is that the injured arterial wall exhibits a reduced hemocompatability compared to that associated with a normal arterial wall. Adverse responses which are associated with reduced hemocompatability include platelet adhesion, aggregation, and activation; potential initiation of the coagulation cascade and thrombosis; inflammatory cell reactions, such as adhesion and activation of monocytes or macrophages; and the infiltration of leukocytes into the arterial wall. Additionally, cellular proliferation results in the release of a variety of growth factors. Restenosis probably results from one or a combination of such responses.

Methods for treating atherosclerosis are disclosed in my U.S. Pat. No. 4,512,762 which issued on Apr. 23, 1985, and which is herein incorporated by reference. This patent discloses a method of injecting a hematoporphyrin into a mammal for selective uptake into the atheromatous plaque, and delivering light to the diseased vessel so that the light activates the hematoporphyrin for lysis of the plaque. However, one of the major problems with such treatments is that the thermal energy does not produce a significant rise in temperature. Also, a flap of material occasionally is formed during the treatment which, after withdrawal of the instrumentation, falls back into the artery, thereby causing abrupt reclosure. This may necessitate emergency coronary artery bypass surgery. Accordingly, such techniques often provide only a temporary treatment for symptoms associated with arterial atherosclerosis.

My U.S. Pat. No. 4,799,479 was issued on Jan. 24, 1989 and is also herein incorporated by reference. This patent discloses a method used in percutaneous transluminal coronary angioplasty wherein a balloon is heated upon inflation. Disrupted tissues of plaque in the arterial wall are heated in order to fuse together fragmented segments of tissue and to coagulate blood trapped with dissected planes of tissues and within fissures created by the fracture. Upon subsequent balloon deflation, a smooth cylindrically shaped channel results. Such heating in that disclosure, however, is used to bond tissue to tissue—not to bond a bioprotective material to tissue.

Approaches such as those disclosed in U.S. Pat. Nos. 4,512,762 and 4,799,479, however, are directed mainly to producing an enhanced luminal result wherein a smooth luminal wall is produced. Problems of biocompatability, including thrombosis, and proliferation of cells tend to remain. Accordingly, the need has arisen to enable a physician to treat patients having atherosclerosis so that the problems of reduced hemocompatability and restenosis are avoided.

As a result of problems remaining unsolved by prior art approaches, there has been a growing disappointment in the cardiology community that until now, no new technology or procedure has been available to dramatically reduce the rate of restenosis.

SUMMARY OF THE INVENTION

The present invention solves the above and other problems by providing a method for treating an arterial wall which has been injured during an angioplasty procedure. The method comprises the steps of positioning an angioplasty catheter adjacent to a lesion to be treated. A soluble transporting medium in the form of a gel which carries a bioprotective material is delivered between the arterial wall and the angioplasty catheter so that the transporting medium and the bioprotective material are entrapped therebetween and permeate into fissures in the arterial wall during apposition thereto of the angioplasty catheter. To liquify the transporting medium and bond the bioprotective material to the arterial wall and within the tissues, thermal energy is applied to the lesion. After removal of the angioplasty catheter, the bioprotective material remains adherent to the arterial wall and within the tissues, thereby providing localized drug therapy and, if desired, coating the luminal surface of the arterial wall with an insoluble layer of the bioprotective material. As a result, at least semi-permanent protection is imparted to the arterial wall, despite contact with blood flowing adjacent thereto. Such blood flow carries away the dissolved transporting medium.

The objects, features, and advantages of the present invention are readily apparent from the following detailed description of the best modes for carrying out the invention when taken in connection with the accompanying drawings.

BEST MODES FOR CARRYING OUT THE INVENTION

The method taught by the present invention can best be appreciated after a preliminary discussion of what now are conventional angioplasty procedures.

Figure 1A:
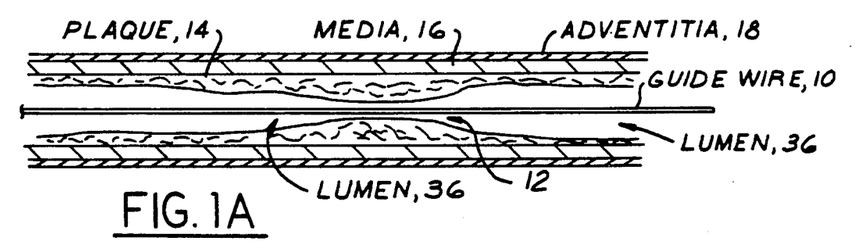
FIG. 1A is a cross-sectional View of a lesion to be treated by a percutaneous transluminal angioplasty procedure, in which plaque is formed within an artery.

FIG. 1A shows a guide wire 10 used in such procedures which is inserted along an artery and through a region 12 which is occluded primarily by plaque 14. Surrounding the plaque 14 are media 60 and adventitia 18. As is now known, the plaque 14 forms an occlusion. The guide wire 10 is usually a stainless steel wire having tightly coiled, but flexible springs. Traditionally, the catheter 20 is made of a plastic, or an elastomeric material and is disposed around the guide wire 10. Following conventional angioplasty, the balloon section 22 is maneuvered so as to lie adjacent to the plaque 14.

Figure 1B:
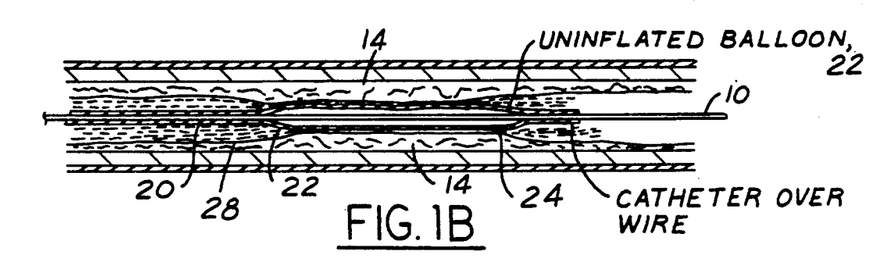
FIG. 1B is a cross-sectional view of the procedure disclosed by the present invention, in which a transporting medium and bioprotective material are delivered to a lesion during distention of an uninflated balloon.

FIG. 1B illustrates the positioning of the uninflated balloon 22 after conventional angioplasty has been performed. Expansion of the balloon 22 to position 22' (FIG. 1C) stretches out the lesion by tissue pressure. Larger balloons are capable of applying more pressure. Between about half an atmosphere and ten atmospheres may be necessary to dilate balloon 22' within the luminal surface 29. Before the balloon 22' is fully expanded, its pressure approximates the tissue pressure. However, once the balloon 22' cracks the plaque and is fully expanded, the outer layers of the tissue are somewhat elastic and the tissue pressure therefore no longer approximates the balloon pressure.

Figure 1C:
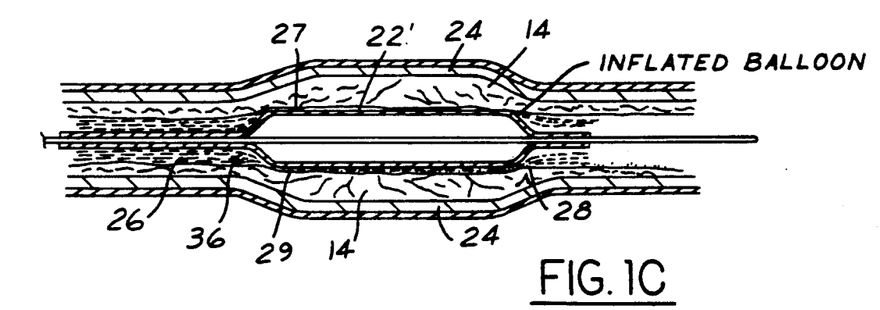
FIG. 1C is a cross-sectional view of the procedure disclosed by the present invention, in which the balloon is inflated and the transporting medium and bioprotective material are entrapped between the balloon and the arterial wall, the transporting medium and the bioprotective material also entering vessels of the arterial wall and fissures which result from previously administered angioplasty procedure.

Referring now to FIG. 1C, the balloon section 22 having been placed adjacent to the plaque 14, is inflated to position 22', thereby opening the artery. At the same time, the fissures and dissected planes of tissue 24 are also opened.

After the catheter 20 is removed, following the teachings of conventional angioplasty procedures, the plaque 14 can collapse into the center of the artery, thereby resulting in an abrupt reclosure of the artery and the possibility of an acute myocardial infarction.

Following prior art techniques, even less severe disruptions in the arterial wall commonly result in gradual restenosis within three to six months after conventional balloon angioplasty. This occurs in part because platelets adhere to exposed arterial tissue surfaces. FIG. 1C is helpful in illustrating the fissures or dissected planes of tissue 24 which result from conventional angioplasty procedures. The presence of regions of blood flow separation and turbulence within the arterial lumen 36 predispose to microthrombi deposition and cellular proliferation within the arterial wall 28.

Figure 4A:
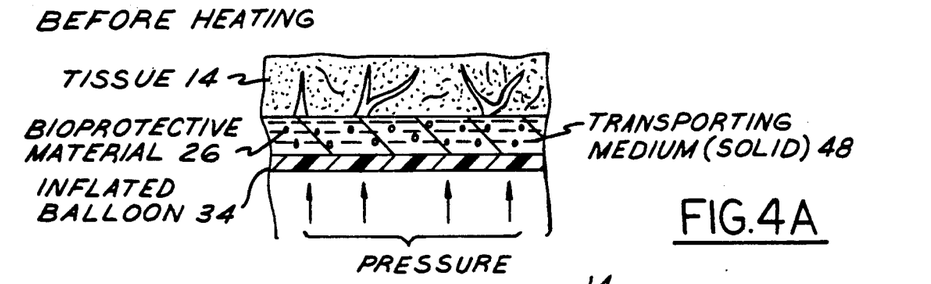
FIGS. 4A-E depict the main process steps involved in practicing the disclosed method for treating the injured arterial wall.

To overcome these and other problems resulting from prior art approaches, the method of the present invention depicted in FIGS. 4A-4E calls for application of the transporting medium 48 and bioprotective material 26 to a lesion 27 of the luminal surface 29 of the arterial wall 28 and to deeper surfaces lining fissures and vessels of the arterial wall. The angioplasty catheter or balloon 20 is first positioned adjacent to the lesion 27 being treated. Next, a sleeve of the transporting medium 48 and bioprotective material 26 is disposed on the angioplasty catheter 20. The sleeve is then delivered to the arterial wall 28, to which it is pressed by inflation of the balloon angioplasty catheter 20 (FIG. 4A). Before completing inflation of the balloon, the transporting medium 48 and bioprotective material 26 lie within fissures and vessels of the arterial wall, between it and the angioplasty catheter 20. During apposition of the angioplasty catheter 20 to the arterial wall 28, a layer of the solid or gelatinous transporting medium 48 and insoluble bioprotective material 28 is entrapped therebetween. Because of pressure exerted radially outwardly by the balloon 34, the transporting medium 48 and bioprotective material 26 further penetrate and permeate the vessels of the arterial wall as well as the fissures and dissected planes of tissue 24. As a result, localized delivery of the bioprotective material 26 occurs.

Figure 4B:
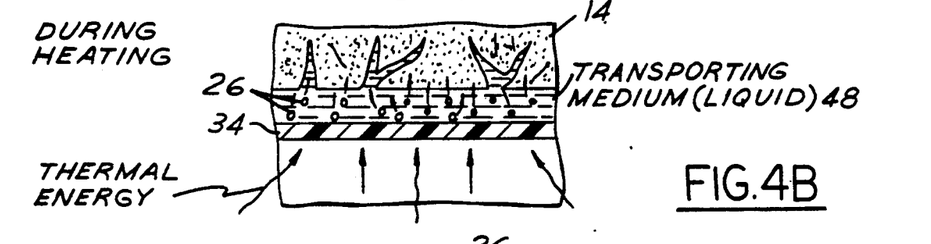

Application of thermal energy, as shown in FIG. 4B, liquifies the soluble transporting medium 48. Urged by mechanical pressure exerted by the inflated balloon 20, and liquification of the transporting medium 48 the insoluble bioprotective material 26 migrates further into the fissures and dissected planes of tissue 24 upon heating. Some of the bioprotective material 26 establishes contact with the luminal surface of the arterial wall 28.

Figure 4C:
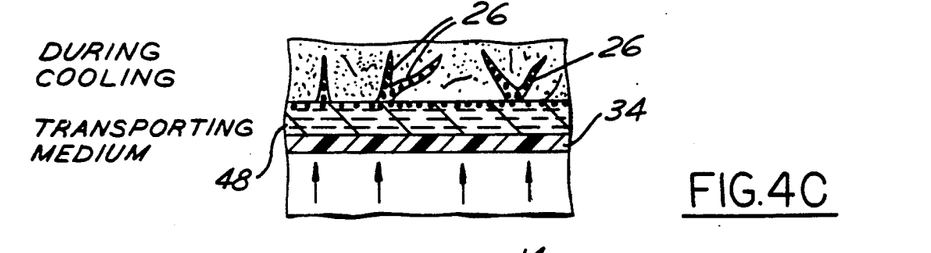
Figure 4D:
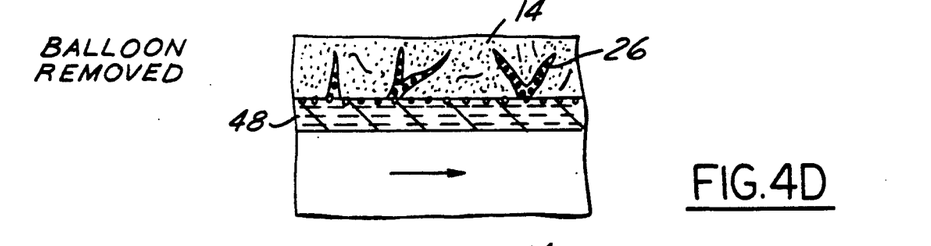
Figure 4E:
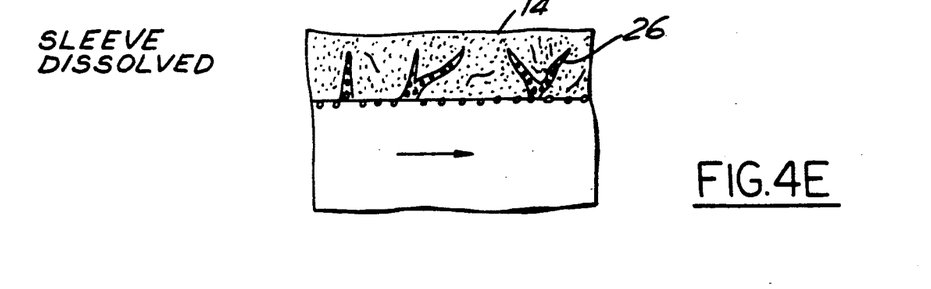

Upon cooling, the transporting medium 48 re-solidifies (FIG. 4C). The bioprotective material 26 becomes bonded to the fissures and along the luminal surface of the arterial wall 28. When the balloon angioplasty catheter 34 is removed (FIG. 4D), the coursing of blood adjacent to the soluble transporting medium 48 results in dissolution and removal thereof (FIG. 4E).

In the treatment method disclosed by the present application, the transporting medium 48 is preferably a soluble gelatin film which is fabricated in the form of a sleeve before placement on the external surface of the balloon 22. Alternatively, the transporting medium 48 may be prepared from a soluble collagen, or heparin in the form of a viscous gel. One or more bioprotective materials 26, including pharmacologic agents, either free or bound to the insoluble carrier, are impregnated within the sleeve. During treatment, inflation of the balloon 22 places the transporting medium 48 and bioprotective material 26 in contact with the arterial tissue.

Upon balloon deflation, the liquified transporting medium 48 rapidly disappears from the luminal surface of the tissue because of its solubility. As a result, the origin of adjacent side branches remain open, since the impregnated bioprotective materials 26, now bonded to the tissue, provide no mechanical support. The bonded bioprotective materials 26 remain at the luminal surface of the tissue by virtue of thermal bonding and their insoluble nature.

Unlike conventional approaches which may require repeated application of the angioplasty procedure with intermittent inflation of the balloon to avoid prolonged interruption of blood flow, the procedure taught by the present invention does not require multiple inflations, and is applied only once for about a twenty second period of thermal treatment followed by about a twenty second period of cooling before balloon deflation. If required, the disclosed technique can be used repeatedly.

Figure 3:
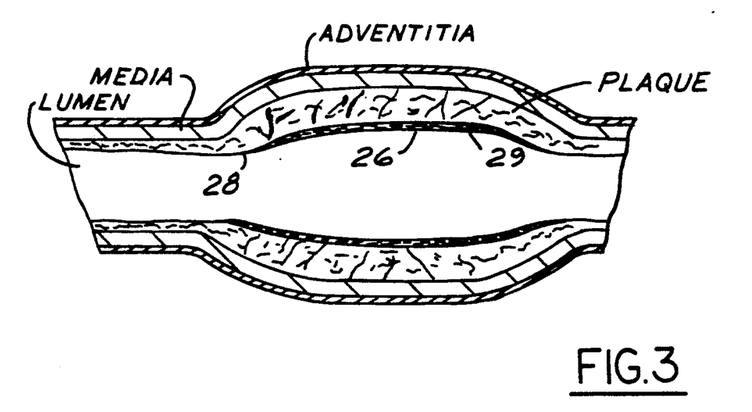
FIG. 3 is a cross-sectional view of the result of utilizing the procedure of the present invention, illustrating a smooth channel formed by the insoluble layer of bioprotective material within sealed fissures and sealed vessels of the arterial wall, thereby providing at least semi-permanent protection to the arterial wall, despite contact with blood flowing adjacent thereto.

Referring now to FIG. 3, after removing the angioplasty catheter 20, and dissolution of the transporting medium 48, the bioprotective material 26 remains adherent to the arterial wall 28. As a result, the luminal surface 29, fissured tissues, and vessels of the arterial wall are coated with an insoluble layer of the bioprotective material 26. The insoluble layer provides at least semi-permanent protection to the arterial wall 28, despite contact with blood flowing adjacent thereto.

It will be appreciated that until the invention disclosed herein, there existed no technique for coating the luminal surface and deeper tissue layers of arteries with a bioprotective material after injury sustained in conventional angioplasty.

As a result of the contribution made by the present invention, it is now possible to coat the luminal surface and deeper layers of injured arteries with insoluble, and therefore permanent or semi-permanent bioprotective materials. One or more of such bioprotective materials could, depending upon the physician's preference, be pharmacologically active. Thrombogenic, inflammatory, or proliferative adverse reactions, or other adverse reactions which normally occur after angioplasty may therefore be reduced. As a result, both short and long term luminal results are improved.

In a preferred method of practicing the present invention, thermal energy is applied to the lesion to bond the bioprotective material 26 to the arterial wall using laser balloon angioplasty (LBA). In this procedure, heat (including heat emanating from non-laser energy sources) and pressure are applied simultaneously to remodel the arterial lumen. The protective biocompatible layer 26 can then be applied to the luminal surface and deeper layers of the arterial wall in ways which are not possible with any other type of angioplasty procedure.

Figures 2, 2A:
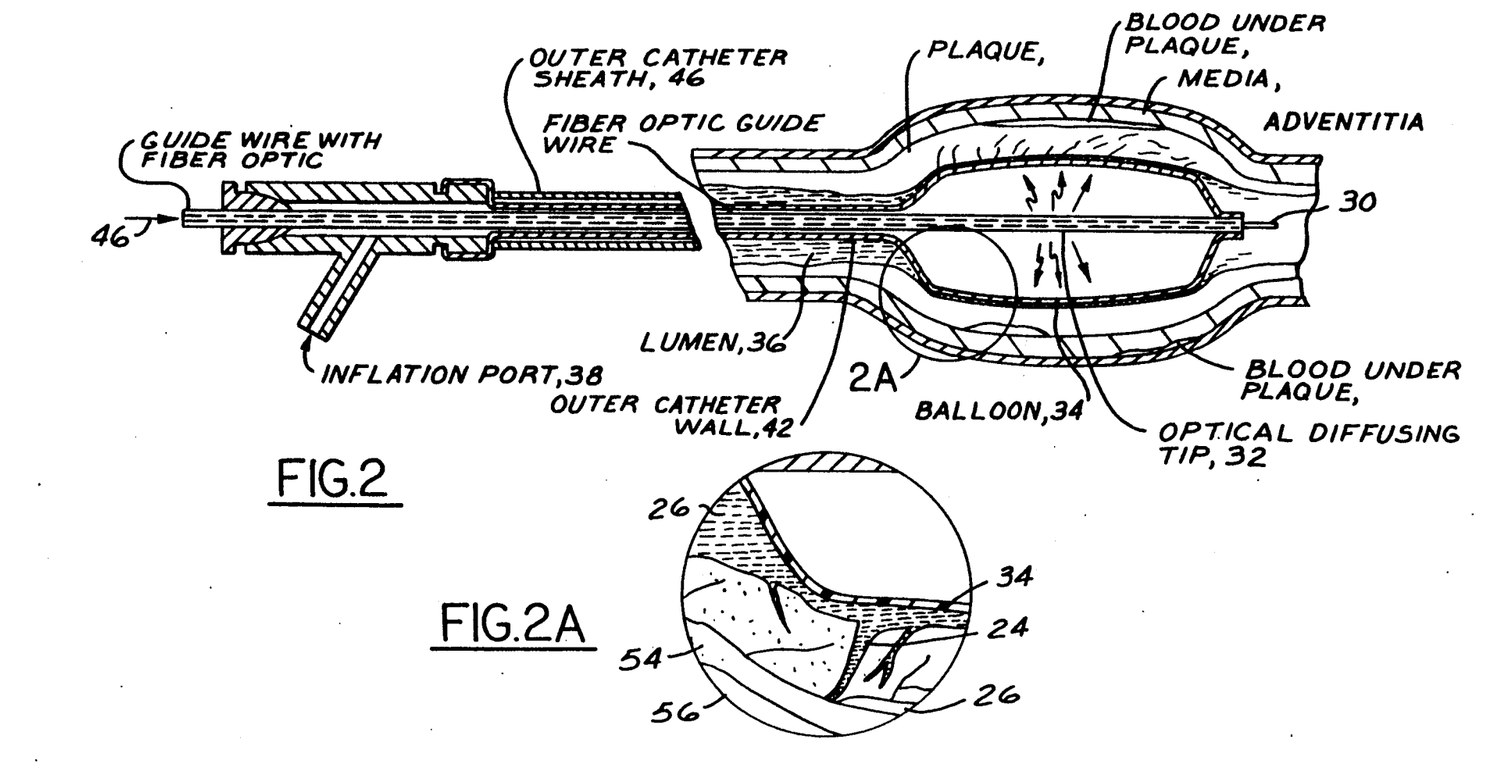
FIG. 2 is a cross-sectional view of one embodiment of the anatomical environment and apparatus used to practice the subject invention, in which the area immediately surrounding the inflated balloon is permeated by the transporting medium bioprotective material, the latter being bonded by thermal energy within the arterial wall being treated, the former being liquified by the thermal energy.
FIG. 2A is an enlarged portion of the circled area depicted in FIG. 2.

Turning now to FIGS. 2 and 4B, it may be seen that thermal energy generated from an optical diffusing tip 32 is represented schematically by radially emanating wavy lines. The thermal energy liquifies the transporting medium 48 and bonds the bioprotective material 26 to the arterial wall 28 and within the tissues 24.

The guide wire 10 may be replaced with an optical fiber 30 having an optical diffusion area or tip 32 located within the inflated balloon 22'. The catheter 20 is inserted around the optical fiber in lumen 36. Expansion of the balloon 22 is produced by a transparent fluid through inflation port 38 in termination apparatus generally located at 40. The fluid utilized for inflation of the balloon may be a contrast medium or crystalloids, such as normal saline, or five percent dextrose in water. Each is relatively transparent to such thermal energy as radiation. After passing through the catheter wall 42, the fluid continues through a channel 44 in the outer catheter sheath, thereby inflating the balloon 34. After inflation, for example, laser radiation 46 is introduced into the optical fiber 30 for transmission to the optical diffusion tip 32. The laser radiation is then diffused therefrom and impinges upon the transporting medium 48 and bioprotective material 26 and the arterial wall 28 after fracture or dissection of the plaque 14 has occurred following prior angioplasty.

It will be apparent that there exist a variety of ways to deliver thermal energy to the area to be treated. Microwave, radio-frequency, or electrical heating of the fluid each are possible techniques.

A preferred technique calls for the use of albumin as the bioprotective material 26. The albumin precipitates onto and is bonded to the luminal surface 29 and deeper layers of the arterial wall as a result of thermal denaturation. It will be appreciated that other types of potentially injectable, heat-transformable materials may be used. Such materials include high molecular carbohydrates such as starch and dextran, liposomes, platelets, red blood cells, fibrinogen, and collagen.

Chemically or thermally cross-linked albumin has been used by others to coat surfaces of prosthetic vascular grafts in order to provide a non-thrombogenic layer. Since a bonded layer of albumin is insoluble, it may persist on the luminal surface for at least four weeks before disappearance. By that time, the surface may be completely healed with a new confluent layer of in-growing endothelial cells, which typically takes about two weeks.

It is also possible to use one or more of a wide variety of therapeutically useful pharmaceutical agents coupled to the albumin, thus providing local drug therapy to prevent restenosis of the angioplastied lesion. Examples of such drugs include anticoagulants (e.g. heparin, hirudin, anti-platelet agents, and equivalents), fibrinolytic and thrombolytic agents, anti-inflammatory agents (e.g. steroidal and non-steroidal compounds), and anti-proliferative compounds (e.g. suramin, monoclonal antibodies to growth factors, and equivalents). Drugs may be bound covantly to albumin in solution, prior to injection, so the drug will be permanently fixed to the heat-precipitated layer of albumin.

Also considered within the scope of the present invention is the use of a bioprotective material or drug 26 which is physically and/or chemically trapped within or by the precipitated layer of albumin. Microspheres 26 could be fabricated in vitro to trap virtually any type of drug therewithin prior to injection into the lumen of the artery. In such an environment, the rate of diffusion of the drug through the walls of the microspheres could be adjusted by the degree of albumin cross-linking induced thermally or chemically. With a currently well-developed technology of fabrication of albumin microspheres, the half life for diffusion of entrapped drugs from the microspheres can be varied from minutes to many months. The dimensions of the microspheres can be made to be smaller than 3 microns, thereby avoiding the problem of capillary plugging. When the drug-containing albumin microspheres is injected into the artery, with or without albumin, thermal cross-linking during thermal exposure will induce adherence of the microspheres to the arterial wall.

Similar concepts could also be applied to a wide variety of other types of microencapsulated drug preparations delivered by the transporting medium 48. The encapsulating medium may consist of liposomes, both high and low molecular weight carbohydrates, sulfated polysaccharides, platelets, red blood cells, gelatin, fibrin, inorganic salts, phosphate glasses, and synthetic polymeric materials. Examples of synthetic polymeric materials include glycoside, lactide, silicone, polyvinylpyrrolidone, poly (methyl methacrylate), and polyamide polymers; ethylene-vinyl acetate copolymer; polyesters such as polyglactin, vicryl, Dexon, and polydioxanone polymers; and hydrogels, such as poly (hydroxyethyl methacrylate), polyacrylamide, polyvinyl alcohol, and gamma-irradiated polyelectrolytes. Additionally, endogenous platelets, removed from the same patient to be treated, can be made to incorporate virtually any water-soluble drug. It should be noted that thermal denaturation of proteins on the surface of a platelet during application of this blood element to the arterial wall can be expected to prevent the platelet from functioning normally as an initiator or promotor of thrombus formation.

Microspheres of any material, when injected along with an albumin solution, or macroaggregated albumin would be similarly trapped with heat-induced precipitation and cross-linking of the albumin. Alternatively, the microcapsules could be thermally bonded directly to tissues, without the use of any additional cross-linkable material. Microcapsules could also be formed in situ at the sleeve-tissue interface as a result of heating the bioprotective material in solution. A water soluble drug which is injected simultaneously with the bioprotective material in solution would thereby become encapsulated upon thermal treatment.

Both water soluble and water-insoluble drugs may be encapsulated within the microspheres. In addition to anti-coagulants, thrombolytic, fibrinolytic, anti-inflammatory, or anti-proliferative agents, other potentially useful drugs or materials may be encapsulated. Examples include immunosuppressant agents (cyclosporin; alkylating agents; adriamycin; and equivalents), glycosaminoglycans (heparin sulfate; dermatan sulfate and equivalents), collagen inhibitors (colchicine; B-aminoproprionitrile; D-penicillamine; 1, 10 phenanthroline, and equivalents), and endothelial cell growth promoters. In addition, a chromophore may be encapsulated in order to enhance absorption of electromagnetic radiation.

As discussed earlier, in addition to the pharmacologic benefit of the invention, cracks and recesses within the mechanically injured arterial wall are filled in with the insoluble material, thereby producing a smoother and, hence, less thrombogenic luminal surface.

A further benefit of the invention results from the drugs being delivered throughout the full thickness of the plaque and arterial wall.

Disclosure of the invention thus far has contemplated administering the bioprotective material 26 as a thin sleeve of a transporting medium, 48 with such material to the external surface of the LBA balloon. The thin sleeve is then transferred to the luminal surface as a result of heat and pressure.

As an example of the preferred embodiment of the invention, a solution of about 5 grams of powdered gelatin in 100 cc's of water was prepared. Heparin at a final concentration of greater than 1000 units per cc was dissolved in the gelatin solution. Gelatin has been found to possess excellent mechanical characteristics, including flexibility and tensile strength for the desired application. Virtually any agent or drug carrier can be impregnated within the film by addition of the bioprotective material before dehydration of the gelatin solution. Dehydration occurs after the transporting medium 48 and the bioprotective material 26 are placed between sheets of, for example, silicone rubber and polyethelene. Dry gelatin films are then produced with a thickness ranging between about 5 to 200 microns. The gelatin films are then mounted on the surface of a laser balloon angioplasty catheter.

Good results have been obtained when a thin lipid coating is applied to the external surface of the mounted film to prevent premature dissolution before deployment. To prevent premature dissolution, the gelatin may also be lightly cross-linked by exposure to a vapor of 50% glutaraldehyde for several minutes or by the use of succinylated gelatin. If the latter approaches are not used, a protective sheath 64 (FIG. 1C) applied to cover the gelatin sleeve 26 during advancement of the balloon 22 to the lesion to be created. After the protective sheath is withdrawn, the sleeve of transporting medium 48 and bioprotective material 26 may then be thermally transferred to the arterial wall.

When the film is heated to about 80°-100° C. for 20 seconds, the gelatin (and lipid coating) melt, thereby allowing the impregnated bioprotective material 26 to contact and bond to the tissue surface.

If either erythrocytes or albumin microspheres are embedded within the gelatin film, exposure of the film, sandwiched between the exposed medial surface of porcine aortic sections and polyethylene terepthalate balloon material to 90°-100° C. in a water bath resulted in liquefaction of the gelatin. Accordingly, the suspended materials within the gelatin were allowed to contact the tissue. The liquified gelatin then disappeared within about one minute at 37° C. in a water bath as a result of the dissolution, leaving the insoluble bioprotective material thermally bonded to the tissue.

It will thus be apparent that the invention contemplates the application of a bioprotective layer 26 to the arterial wall 28, wherein the bioprotective layer 26 is pharmacologically active and delivers high concentrations of drugs locally, so that problems of systemic toxicity are circumvented. In practicing the disclosed invention, DNA fragments or genes can be transferred to the arterial wall. Adherence of such genetic material, either alone or carried by the transporting medium 48 to the arterial wall, is induced by thermal energy. Preferably, the genetic material is incorporated within a balloon-transferrable sleeve, such as gelatin.

DNA from a wide variety of species exhibits a discrete temperature at which it denatures, corresponding to its melting point, which exceeds 80° C. for nearly all species. Since thermal bonding of drug carriers such as erythrocytes and liposomes can be achieved at lower temperatures, adherence of the carriers to the arterial wall can be induced without damaging the genetic material entrapped therewithin. Enzyme(s) produced by the transferred genes would be released close to the luminal surface. In such cases, a relatively high local blood concentration of an enzyme such as tissue plasminogen activator would serve to prevent arterial thrombosis at the site of release, as well as distal to the site. Alternatively, genes which release enzymes for replacement in patients with genetic deficiencies could be applied in high concentration over a broad luminal surface area, so that systemically useful levels are achieved. Advantages of the approach include its rapidity, so that tissue ischemia during balloon inflation is not problematic, and the ability to deliver a large quantity of genetic material directly to a relatively small surface area of the vessel to be treated.

While the preferred method of applying thermal energy is the use of electromagnetic radiation, including laser, electrical resistive, radio-frequency, and microwave energy sources, alternative methods may be used. Such methods include chemical and ultrasonic techniques. Moreover, externally focussed energy sources directed inwardly, including ultrasonic and microwave energy, could alternatively be used to heat the balloon, arterial wall, or bioprotective material without the use of an energy-delivering catheter.

There has been provided in accordance with the invention a method for applying bioprotective materials to the luminal surface and arterial wall during balloon angioplasty which addresses the needs and solves the problems remaining from conventional approaches. By practicing the disclosed method, high concentrations of drugs can be delivered to a site to be treated. Additionally, their thickness and confluence can be controlled. Since the drug or drug carrier provide no mechanical support to the injured vessel after the transporting medium is washed away, any microspheres of bioprotective material that becomes dislodged will not obstruct flow because of their small size While the invention has been described in conjunction with specific modes for practicing the invention, it is evident that many alternatives, modifications, and variations will be apparent to those skilled in the art in light of the foregoing description. Accordingly, it is intended to embrace all such alternatives, modifications, and variations as fall within the spirit and broad scope of the following claims.

What is claimed is:

1. A method for treating a lesion in an arterial wall having plaque thereon and a luminal surface, the arterial wall having been injured during an angioplasty procedure, the arterial wall and the plaque defining therewithin fissures resulting therefrom, the method comprising the steps of:

providing a layer of a transporting medium disposed about an angioplasty catheter balloon, said transporting medium having a bioprotective material distributed therewithin, the layer of bioprotective material being surrounded by a removable sheath to prevent premature dissolution of the bioprotective material;

positioning the angioplasty catheter adjacent to the lesion being treated so that the transporting medium and the bioprotective material are entrapped therebetween;

removing the sheath so that the lesion is exposed to the bioprotective material;

applying thermal energy, thereby liquefying the transporting medium under pressure and promoting contact of the bioprotective material with the fissures and the luminal surface, whereby the thermal energy bonds the bioprotective material to the arterial wall and within the fissures and vessels of the arterial wall; and removing the angioplasty catheter, the bioprotective material remaining adherent to the fissures and vessels within the arterial wall, thereby treating the injured luminal surface with the bioprotective material, whereby at least semi-permanent protection to the arterial wall is provided, despite contact with blood flowing adjacent thereto, the blood dissolving and removing the transporting medium.

2. The method of claim 1 wherein the angioplasty catheter utilized includes an inflatable balloon.

3. The method of claim 2 wherein the inflatable balloon is at least partially inflated before delivering the transporting medium and bioprotective material between the arterial wall and the inflatable balloon, thereby promoting localized application of the bioprotective material to the arterial wall.

4. The method of claim 1 wherein the bioprotective material utilized is a macroaggregated albumin which bonds to the luminal surface and within fissures and vessels of the arterial wall as a result of the application of thermal energy.

5. The method of claim 1 wherein the bioprotective material comprises platelets carried by the transporting medium, which become adherent to the luminal surface and to tissues adjacent to fissures and vessels of the arterial wall as a result of the application of thermal energy.

6. The method of claim 1 wherein the bioprotective material comprises red blood cells carried by the transporting medium, which become adherent to the luminal surface and to tissues adjacent to fissures and vessels of the arterial wall as a result of the application of thermal energy.

7. The method of claim 1 wherein the bioprotective material comprises liposomes carried by the transporting medium, which become adherent to the luminal surface and to tissues adjacent to fissures and vessels of the arterial wall as a result of the application of thermal energy.

8. The method of claim 1 wherein the transporting medium comprises a gelatin which liquifies upon application of thermal energy, whereby the bioprotective material within the liquified transporting medium bonds to the luminal surface and within fissures and vessels of the arterial wall as a result of the application of thermal energy.

9. The method of claim 1 wherein the bioprotective material utilized bonds to the luminal surface and within fissures and vessels of the arterial wall as a result of the application of thermal energy.

10. The method of claim 1 wherein the bioprotective material comprises a high molecular weight carbohydrate which bonds to the luminal surface precipitates onto the luminal surface and within fissures and vessels of the arterial wall as a result of the application of thermal energy.

11. The method of claim 1 wherein the bioprotective material utilized entraps a useful pharmaceutical agent in order to provide local drug therapy directly to the luminal surface, and to fissures defined within the arterial wall.

12. The method of claim 11 wherein the useful pharmaceutical agent is an anti-coagulant.

13. The method of claim 11 wherein the useful pharmaceutical agent is a fibrinolytic agent.

14. The method of claim 11 wherein the useful pharmaceutical agent is a thrombolytic agent.

15. The method of claim 11 wherein the useful pharmaceutical agent is an anti-inflammatory agent.

16. The method of claim 11 wherein the useful pharmaceutical is an anti-proliferative compound.

17. The method of claim 11 wherein the useful pharmaceutical is an immunosuppressant.

18. The method of claim 11 wherein the useful pharmaceutical is a collagen inhibitor.

19. The method of claim 11 wherein the useful pharmaceutical is an endothelial cell growth promotor.

20. The method of claim 11 wherein the useful pharmaceutical is a sulfated polysaccharide.

21. The method of claim 1 wherein the bioprotective material includes a drug which is bound to albumin prior to injection, so that the drug is permanently affixed thereto by application of the thermal energy.

22. The method of claim 1 wherein the bioprotective material includes a drug which is physically trapped within albumin during the application of thermal energy.

23. The method of claim 1 wherein the bioprotective material comprises microspheres.

24. The method of claim 1 wherein the bioprotective material includes a drug preparation having an encapsulating medium.

25. The method of claim 24 wherein the encapsulating medium comprises albumin.

26. The method of claim 24 wherein the encapsulating medium comprises carbohydrates.

27. The method of claim 24 wherein the encapsulating medium comprises platelets.

28. The method of claim 24 wherein the encapsulating medium comprises liposomes.

29. The method of claim 24 wherein the encapsulating medium comprises red blood cells.

30. The method of claim 24 wherein the encapsulating medium comprises gelatin.

31. The method of claim 24 wherein the encapsulating medium comprises hemoglobin.

32. The method of claim 24 wherein the encapsulating medium comprises a synthetic polymer.

33. The method of claim 24 wherein the encapsulating medium comprises a sulfated polysaccharide.

34. The method of claim 24 wherein the encapsulating medium comprises ghost red cells.

35. The method of claim 24 wherein the encapsulating medium comprises heparin.

36. The method of claim 1 wherein the bioprotective material is a confluent layer of microspheres impregnated on the surface of the transporting medium.

37. The method of claim 1 wherein the step of removing the angioplasty catheter is (followed) by the step of cooling the liquified transporting medium and tissues, thereby enhancing bonding of the bioprotective material to the lesion so that the bioprotective material remains adherent to the arterial wall, and fills cracks and recesses therewithin, thereby providing localized delivery of the bioprotective material.

38. The method of claim wherein the transporting medium becomes re-solidified upon cooling, and is dissolved by blood flowing adjacent thereto after removal of the catheter.

39. The method of claim 1 wherein microspheres are formed in situ at the luminal surface and within the arterial wall as a result of the thermal energy applied to the transporting medium and the bioprotective material.

40. The method of claim 1 wherein a drug, simultaneously injected with the bioprotective material, is entrapped within microspheres.

41. The method of claim 1 wherein the bioprotective material functions as a physiologic glue, thereby enhancing thermal fusion of fissured tissues within the arterial wall.

42. The method of claim 1 wherein the bioprotective material includes a chromophore which enhances absorption of electromagnetic radiation.

43. The method of claim 24 wherein the encapsulating medium comprises a chromophore which enhances absorption of electromagnetic radiation.

44. The method of claim 1 wherein the angioplasty catheter is a metal probe.

45. The method of claim 1 wherein the applied thermal energy is electromagnetic radiation.

46. The method of claim 45 wherein the applied thermal energy is continuous wave electromagnetic radiation.

47. The method of claim 45 wherein the applied thermal energy is pulsed electromagnetic radiation.

48. The method of claim 45 wherein the electromagnetic radiation is laser radiation.

49. The method of claim 45 wherein the electromagnetic radiation is radio-frequency radiation.

50. The method of claim 45 wherein the electromagnetic radiation is microwave radiation.

51. The method of claim 45 wherein the electromagnetic radiation is generated from electrical resistance.

52. A method for treating a lesion in an arterial wall having plaque thereon and a luminal surface, the arterial wall and the plaque defining therewithin fissures resulting therefrom, the method comprising the steps of:

performing angioplasty;

providing a layer of a transporting medium disposed about an angioplasty catheter balloon, said transporting medium having a bioprotective material distributed therewithin, the layer of bioprotective material being surrounded by a removable sheath to prevent premature dissolution of the bioprotective material;

positioning the angioplasty catheter adjacent to the lesion being treated so that the transporting medium and the bioprotective material are entrapped therebetween;

removing the sheath so that the lesion is exposed to the bioprotective material;

applying thermal energy, thereby liquefying the transporting medium under pressure and promoting contact of the bioprotective material with the fissures and the luminal surface, whereby the thermal energy bonds the bioprotective mate rail to the arterial wall and within the fissures and vessels of the arterial wall; and removing the angioplasty catheter, the bioprotective material remaining adherent to the fissures and vessels within the arterial wall, thereby treating the injured luminal surface with the bioprotective material, whereby at least semi-permanent protection to the arterial wall is provided, despite contact with blood flowing adjacent thereto, the blood dissolving and removing the transporting medium.

53. The method of claim 1 wherein the step of applying thermal energy to the lesion comprises applying the thermal energy from the angioplasty catheter radially outwardly.

54. The method of claim 1 wherein the step of applying thermal energy to the lesion comprises the step of applying thermal energy so that the temperature within the bioprotective material is raised to at least 40° C.

55. The method of claim 1 wherein the transporting medium is a soluble gelatin film.

56. The method of claim 55 wherein the gelatin is removed from the luminal surface of the tissue by ambient blood flow upon removal of the angioplasty catheter.

57. The method of claim 1 wherein the layer of a transporting medium has a thickness between about 5-200 microns.

58. The method of claim 11 wherein the useful pharmaceutical agent is an inhibitor of collagen cross-linking.

59. The method of claim 11 wherein the useful pharmaceutical agent is an inhibitor of elastin cross-linking.

60. The method of claim 11 wherein the useful pharmaceutical agent comprises deoxyribonucleic acid.

61. The method of claim 11 wherein the useful pharmaceutical agent material comprises ribonucleic acid.

62. The method of claim 11 wherein the useful pharmaceutical agent comprises one or more genes.

63. A method of treating a lesion in an arterial wall having plaque thereon and a luminal surface, the arterial wall having been injured during an angioplasty procedure, the arterial wall and the plaque defining therewithin fissures resulting therefrom, the method comprising the steps of:

positioning a layer of a transporting medium disposed about an angioplasty catheter balloon, said transporting medium having a bioprotective material distributed therewithin upon a balloon angioplasty catheter adjacent to the lesion being treated, the layer being surrounded by a removable sheath to prevent premature dissolution of the bioprotective material;

removing the sheath so that the lesion is exposed to the bioprotective material;

applying thermal energy to the lesion and inflating the balloon, thereby liquefying the transporting medium and promoting contact of the bioprotective material with the fissures and luminal surface, whereby the thermal energy bonds the bioprotective material to the arterial wall and within the fissures and vessels of the arterial wall;

allowing the transporting medium to cool, thereby enabling it to become re-solidified;

removing the angioplasty catheter, the bioprotective material remaining bonded to the fissures and vessels within the arterial wall, thereby treating the injured luminal surface with the bioprotective material, whereby at least semi-permanent protection to the arterial wall is provided, the blood flowing adjacent thereto, thereby dissolving and removing the resolidified transporting medium.

* * * * *